United States Patent [19]

Osteryoung et al.

[11] Patent Number: 4,846,955
[45] Date of Patent: Jul. 11, 1989

[54] CONTROLLED-GROWTH MERCURY DROP ELECTRODE

[75] Inventors: Janet G. Osteryoung, Amherst, N.Y.; Zygmunt Kowalski, Krakow, Poland

[73] Assignee: The Research Foundation of State University of New York, Albany, N.Y.

[21] Appl. No.: 165,599

[22] Filed: Mar. 8, 1988

[51] Int. Cl.$^4$ ............................................. G01N 27/34
[52] U.S. Cl. ................................. 204/413; 251/129.15
[58] Field of Search ..................... 204/413; 251/129.15

[56] References Cited

U.S. PATENT DOCUMENTS 4,548,679 10/1985 Guidelli et al. ...................... 204/1 T
4,756,331 7/1988 Stegmaier ........................... 137/271

OTHER PUBLICATIONS

James A. Plambeck, "Electroanalytical Chemistry", pp. 27–28, (1982).
W. Peterson, "Static Mercury Drop Electrode", EG&G Application Note T-2.
P. Sturrock and W. Williams, "Modified Static Mercury Drop Electrode", *Anal. Chem.* 2629 (1982).
Z. Kowalski, K. Wong, R. Osteryoung & J. Osteryoung, "Controlled-Growth Mercury Drop Electrode", *Analytical Chemistry*, 1987, 59, 2216 (9/1/87).
K Wong, Z. Kowalski, R. Osteryoung and J. Osteryoung, "A new Controlled-Growth Mercury Drop Electrode", Abstract No. 304, *The Pittsburgh Conference & Exposition on Analytical Chemistry and Applied Spectroscopy* (3/9–13/87).
Z. Kowalski, "Application of a Controlled-Growth Mercury Drop Electrode for Polarography", *Analyst*, vol. 112 (4/1/87).

*Primary Examiner*—G. L. Kaplan
*Attorney, Agent, or Firm*—Robert P. Simpson; Michael L. Dunn

[57] ABSTRACT

A mercury drop electrode for use in electrochemical experiments. The invention includes a reservoir for liquid mercury, a mercury drop capillary having upper and lower open ends and also having a chemically inert lower capillary tube portion and an electrically conductive upper capillary tube portion supported by the lower portion and in contact with the mercury in the reservoir, valve means including a valve stem having a seal at its lower end and a ferromagnetic portion at its upper end, a valve seat comprising the upper end of the upper portion of the capillary which acts in concert with the valve seal to close the valve, and actuating means operatively arranged to lift the valve seal form the seat to allow mercury to enter the capillary from the reservoir and to lower the seal to the seat to prevent mercury from entering the capillary from the reservoir.

29 Claims, 5 Drawing Sheets

CONTROLLED-GROWTH MERCURY DROP ELECTRODE

BACKGROUND OF THE INVENTION

The present invention relates to a controlled-growth mercury drop electrode for use in electrochemical experiments, and more particularly to a valve control for regulating the rate of growth and surface area of the mercury drops. The electrochemical experiments include measurement of, for example, surface tension, current at controlled potential, potential at controlled current or charge, and so on. Voltammetry, a group of techniques involving measurement of current as a function of potential with time as a parameter, is discussed herein as an example of a specific use of the present invention.

In voltammetry, the potential of the working electrode, here a droplet of mercury, is maintained at a known value with respect to a reference electrode placed in the same solution. An electroactive substance in the solution will transfer electrons to, or accept electrons from, the external circuit at the surface of the working electrode if the potential is in a characteristic range. The former process is described as anodic oxidation, the latter as cathodic reduction. The magnitude of the current is proportional to the concentration of the substance in solution; thus voltammetry is used for quantitative analysis. The characteristic potential depends on the identity of the substance; thus it is also used for qualitative analysis.

The volume of solution is typically 1-50 mL, but the electrochemical reaction typically takes place only near the working electrode, and thus the technique is nondestructive. In routine use, the concentration of electroactive material can be determined in the range $10^{-8}$ to $10^{-2}$ M Specialized techniques such as stripping voltammetry permit determinations down to $10^{-}$M in some cases.

Voltammetry is usually carried out with a three-electrode configuration. A potentiostat is employed to control the potential of the working electrode with respect to the reference electrode by forcing the necessary current through an auxiliary electrode. This current also passes through the working electrode and is measured using a current-to-voltage transducer. The control potential is varied according to a specific potential-time program which may consist of a ramp, sine wave, or pulse sequence, for example. The current is sampled, differenced, averaged, or subjected to some other manipulation appropriate to the potential-time program to produce a current output. A plot of current output versus some function of the control potential is called a voltammogram.

Voltammograms are generally S-shaped or peak-shaped. The S-shaped voltammograms are characterized by a limiting current, $i_l$, and a half-wave potential, $E_{\frac{1}{2}}$, (potential at which $i=i_l/2$). Peak-shaped voltammograms are characterized by peak current, $i_p$, and peak position, $E_p$. Either $i_l$ or $i_p$ is a measure of the concentration of reacting material, and $E_{\frac{1}{2}}$ or $E_p$ depends on the fundamental properties of the charge transfer process.

Current within the working electrode may arise from anodic or cathodic reaction or from the process of charging the electrode surface, which behaves like a potential-dependent capacitor. Thus, changes in potential or area require charging current which appears as an unwanted component of the total current when the current due to charge transfer is sought. When mercury is used as the electrode material, it is desirable to measure current at fixed area in order to eliminate the charging current which would arise due to change in area. The charging current due to change in potential decays exponentially with the time constant RC, R being the resistance and C the capacitance of the electrode. Smaller values of RC permit reliable current measurements at shorter times. This is desirable because the current due to charge transfer also decays with time; thus, measurements at shorter times give more signal per unit concentration.

Mercury is a highly desirable electrode material because the liquid surface is readily and reproducibly renewable, in sharp contrast with solid electrode materials. It also has an excellent potential range for carrying out reductions in aqueous solution.

Due to their advantages, mercury drop electrodes are widely used in the field of electrochemical analysis. Prior ar devices have a number of disadvantages, however, which are well-documented in the prior art. For example, to ensure optimum voltammetric results, it is critical to maintain electrical continuity between the mercury in the reservoir and the mercury in the capillary. The resistance of this contact between the mercury in the capillary with that in the reservoir usually is the limiting factor in extending applications of the static mercury drop electrode to measurements at short times. In an attempt to solve this problem, one prior art design includes coating the tip of the capillary with a layer of tin oxide to ensure continuity. However, the mechanical design of the valve of this prior art electrode is such that the relatively massive plunger repetitively pounds the tip of the capillary leading to a deterioration of the tin oxide layer. Also, the tin oxide layer has a significant resistance, and this resistance varies from capillary to capillary depending upon the dimensions of the layer and also varies within one capillary as the oxide layer deteriorates. The present inventors have measured this contact resistance and found it to be in the range 20-70 ohms. Other researchers have measured the resistance and claim values to several hundred ohms. Sturrock and Williams, *Modified Static Mercury Drop Electrode*, 54 Anal. Chem. 2629-31 (1982).

Prior art devices demonstrate other disadvantages as well. For example, one prior art device offers only three different drop sizes. Although fine control of drop surface area over a wide range provides possibilities for optimizing many different procedures on one electrode, for unattended monitoring, and for study of surface relations, this control is not generally available on prior art devices. Prior art electrodes also suffer from poor reproducibility. For example, with one commercially available model, it is difficult to reproduce mercury drop size to better than 3% from day to day. Frequent recalibration of the drop size is necessary for accurate measurements. The drop size must be known to measure the fundamental calibration constant, the diffusion coefficient. It must be maintained constant to achieve constant sensitivity.

Another problem with prior art electrodes is the fact that the housings are generally constructed of opaque material, such as stainless steel. This construction renders it impossible to visually monitor the mercury for contaminants and for proper mercury level. Moreover, it is usually not possible to invert prior art electrodes for the purpose of replacing the capillary, without first draining the mercury from the reservoir, which is a time-consuming operation. Finally, a general problem with prior art devices is that abnormal current-time behavior is obtained when the mercury is flowing out from the capillary. In practice, a waiting time of one second or longer is required for a newly formed mercury drop to stabilize before any current measurement is made.

SUMMARY OF THE INVENTION

The present invention provides a mercury drop electrode for use in electrochemical experiments. The invention broadly includes a reservoir for liquid mercury, a mercury drop capillary having upper and lower open ends. The mercury drop capillary includes a chemically inert lower capillary tube portion and an electrically conductive upper capillary tube portion supported by the lower portion. The upper capillary tube portion is in contact with the mercury in the reservoir. The electrode further includes valve means including a seal, and a valve seat acting in concert with the seal to close the valve. The seat includes the upper end of the upper portion of the capillary. The electrode further includes actuating means to lift the seal from the seat to allow mercury to enter the capillary from the reservoir and to lower the seal to the seat to prevent mercury from entering the capillary from the reservoir.

Accordingly, an overall object of the invention is to provide a novel mercury drop electrode for use in electrochemical experiments.

A more particular object of the invention is to provide a mercury drop electrode having a valve design which provides electrical continuity between the mercury in the reservoir and the mercury in the capillary when the valve is closed.

Still another object of the invention is to provide a mercury drop electrode having a fast-response valve which enables regulation of drop size and rate of growth.

A further object of the invention is to provide a mercury drop electrode which reproduces drop size consistently within 2%.

Yet another object of the invention is to provide a mercury drop electrode having a transparent housing to enable visual monitoring of the mercury.

Yet a further object of the invention is to provide a mercury drop electrode which may be inverted without spillage of mercury for the purpose of replacing a broken capillary.

Still a further object of the invention is to provide a fast-acting valve for a mercury drop electrode wherein the glass capillary is insulated from the constant pounding of the pull-rod by an electrical conducting element secured to the capillary.

DETAILED DESCRIPTION OF THE INVENTION

Figure 1:
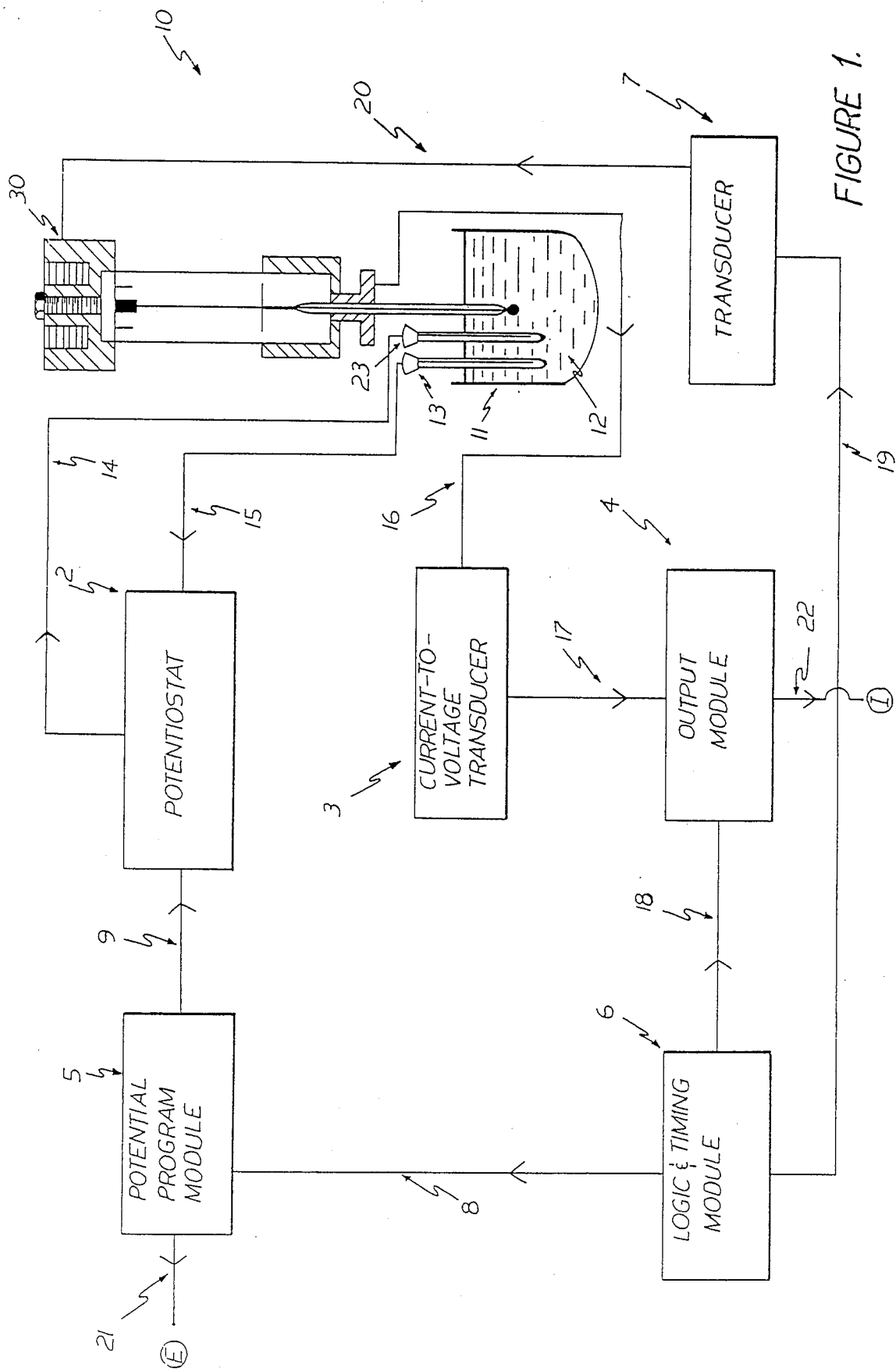
FIG. 1 is a schematic diagram of a typical voltammetric instrument including a cell and electrodes.

At the outset, it should be clearly understood that like reference numerals are intended to identify the same structural elements, portions or surfaces consistently throughout the several drawing figures, as such elements, portions or surfaces may be further described or explained by the entire written specification. Unless otherwise indicated, the drawings are intended to be read (e.g., cross-hatching, arrangement of parts, etc.) together with the specification, and are to be considered a portion of the entire "written description" of this invention, as required by 35 USC 112. As used in the following description, the terms "horizontal," "vertical," "left," "right," "up," and "down," as well as adjectival and adverbial derivatives thereof (e.g., "horizontally," "rightwardly," "upwardly," etc.) refer to the relative orientation of the illustrated structure as the particular drawing figure faces the reader. Similarly, the terms "inwardly" and "outwardly" refer to the orientation of a surface of revolution relative to its axis.

The description of a preferred embodiment is presented herein in conjunction with a description of alternative embodiments.

FIG. 1 is a schematic diagram of a typical voltammetric instrument 10. Test cell 11 contains the fluid 12 to be analyzed. As used herein, the term "fluid" usually refers to a liquid, and most often a chemical solution. Submersed in the fluid are reference electrode 13, working electrode 30 and counter electrode 23. Reference electrode 13 may be a saturated calomel electrode, whereas working electrode 30 represents the controlled-growth mercury drop electrode of the present invention. Counter electrode 23 is an inert current carrier which may be made of platinum. Potentiostat 2 compares the value of the reference electrode potential received from reference electrode 13 via line 15 with the value of the control potential received via line 9 from potential program module 5 and supplies the necessary current through line 14 to counter electrode 23 to force their sum to be zero. In this example, working electrode 30 is at virtual ground and therefore its potential with respect to the potential of reference electrode 13 is equal to the control potential.

The current through working electrode 30 passes via line 16 to current-to-voltage transducer 3, the output of which is transmitted via line 17 to output module 4 which manipulates this voltage signal as appropriate to the experiment. Thus, for example, output module 4 may sample the voltage signal from line 17 at fixed time intervals. Logic and timing module 6 controls the current output module via line 18 and controls the potential program module via line 8. Thus, the current output is synchronized with the potential program. In addition, logic and timing module 6 controls synchronously transducer 7 via line 19. Transducer 7 in turn controls some mechanical aspect of the experiment. In the present case, transducer 7 is embodied in solenoid 60 of FIG. 3 as well as in solenoid 78 of FIG. 3. Line 21 supplies a potential signal E from potential program module 5, and line 22 supplies a current signal I from current output module 4. These are the current and potential signals which, when displayed on a suitable device (e.g., oscilloscope monitor), constitute the voltammogram.

Working electrode 30 is the controlled-growth mercury electrode of the present invention. Described in more detail herebelow, electrode 30 functions to complete the electrical circuit to the fluid by providing a conductive path through the mercury in the reservoir, mercury in the capillary, and mercury drops in contact with the fluid. To maintain an uncontaminated mercury surface in contact with the fluid, mercury drops can be continuously renewed at the lower end of the capillary. The rate of growth and size of the mercury drops are controlled by logic and timing module 6, which provides electrical pulses to the solenoid of electrode 30 via lines 23 and 24. Logic and timing module 6 may be any electronic circuit capable of providing timed electrical pulses, or it may be a computer together with real time clock and interfacing which has been programmed to provide pulses to the solenoid.

Figure 2:
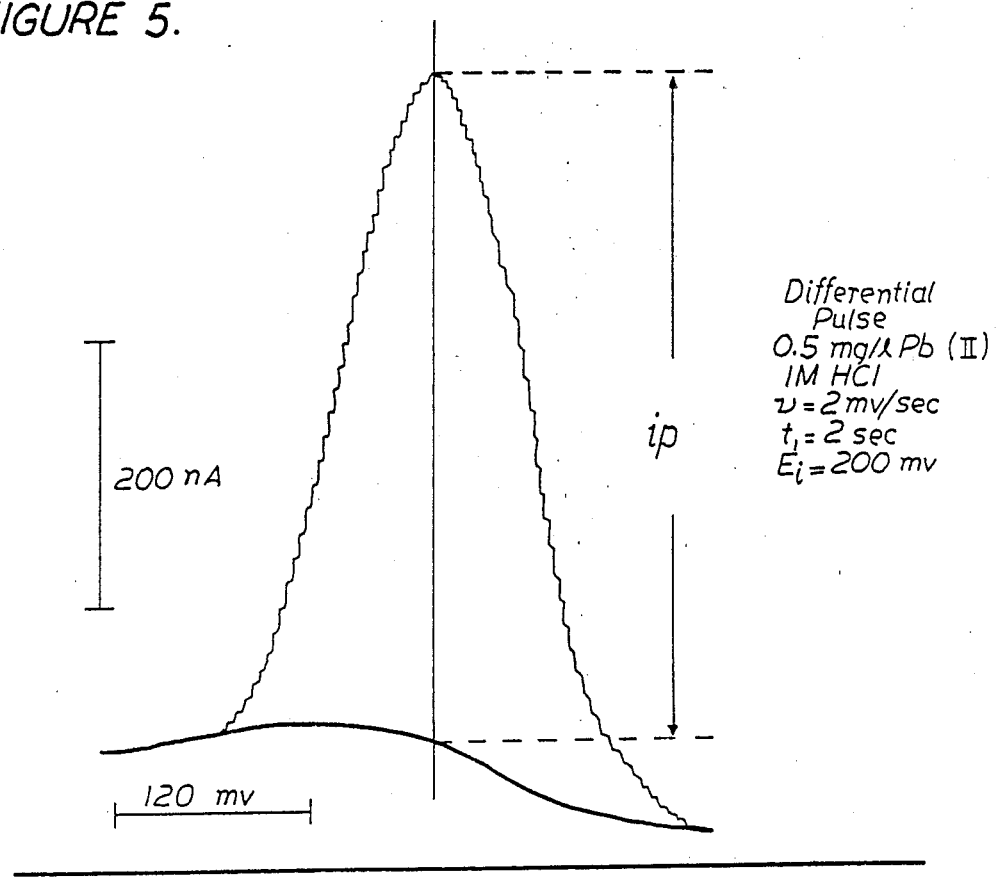
FIG. 2 is a representation of a typical voltammogram.

FIG. 2 represents a typical differential pulse voltammogram. The potential of a mercury electrode is scanned in a linear fashion at 2 millivolts/second from −200 millivolts versus a calomel reference to more negative values. Once every 2 seconds a potential pulse is applied of width 57 milliseconds and amplitude 50 millivolts. The current is sampled 8 milliseconds before the pulse is applied and 48 milliseconds afterward. The current output is the difference of these two values. The lower curve is the capacity current obtained in M HCl. The upper curve is obtained with the addition of Pb(II). The peak current, $i_p$, is the maximum difference between the two and is proportional to the concentration of Pb(II). The position of the peak on the potential scale is characteristic of the reduction of Pb(II) in M HCl to form lead amalgram. Thus, the voltammogram serves to identify the species undergoing electrochemical reaction and to measure the concentration of that species in solution.

Figure 3:
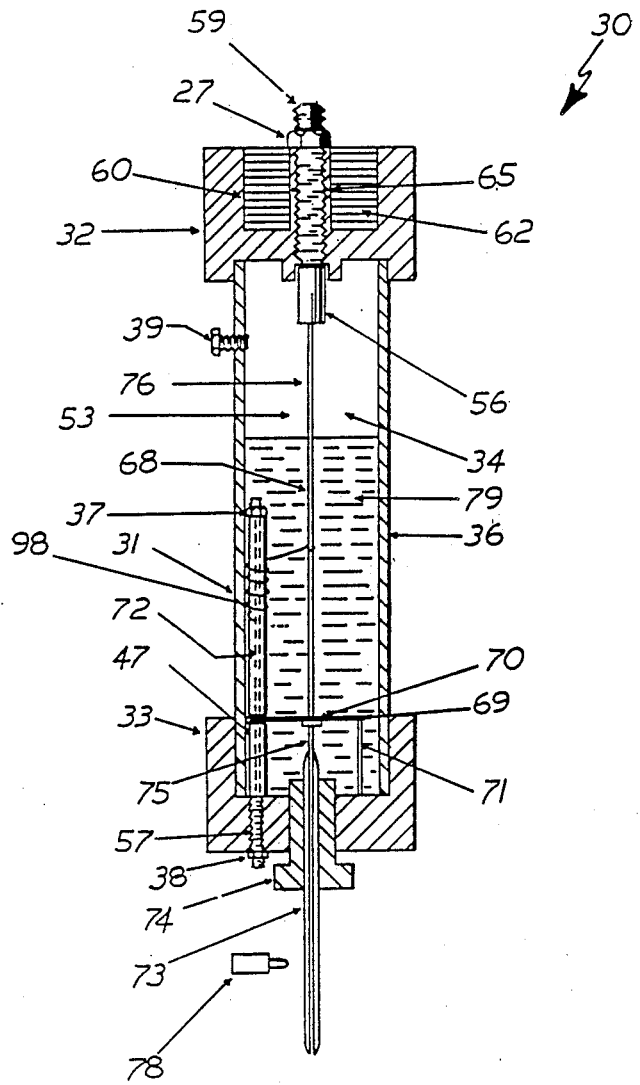
FIG. 3 is a sectional diagram of a preferred embodiment of a controlled-growth mercury drop electrode in accordance with the teachings of the present invention.

FIG. 3 is a sectional view of a preferred embodiment of the controlled-growth mercury drop electrode. FIG. 4 is an exploded sectional view of the electrode illustrated in FIG. 3.

In accordance with the present invention, the controlledgrowth mercury drop electrode 30 illustrated in FIG. 3 comprises a housing 31 which is secured to upper end-cap 32 and lower end-cap 33 so as to form reservoir 34 for liquid mercury 79. Housing 31 is preferably formed of transparent material, such as polypropylene, which must not react with mercury. This transparent housing makes it possible for the operator to monitor the mercury for contaminants, and to maintain a proper level of mercury in the reservoir. It should be understood that other fluids may be substituted for mercury. The fluid must be a conductor of electricity and must not react with the fluid being analyzed. Thus, hereinafter, the term "mercury" is defined to denote mercury and any other fluid substitutable therefor.

With reference to FIG. 3, housing 31 includes cylindrical wall 36, which is threadably engaged with upper end-cap 32 and lower end-cap 33. In a preferred embodiment, the actuating means includes solenoid 60 and valve stem 53, which function cooperatively to open and close the valve. Upper end-cap 32 holds solenoid 60 which includes adjustable ferromagnetic core 59 which is threadably engaged with end-cap 32. Core 59 is adjustable in that it may be partially unscrewed from end-cap 32 to regulate the strength of the electromagnetic field. Lower end-cap 33 is threadably engaged with the lower end of housing 31. Ferrule 74 is threadably engaged with lower end-cap 33. Mercury drop capillary 73 is held in the through-bore of ferrule 74 by any suitable means, such as by epoxy cement. A "mercury drop capillary" is a capillary through which mercury will flow by gravity to form mercury droplets at its lower opening. Filling cap 39 is threadably engaged with wall 36 and may be unscrewed to permit filling reservoir 34 with mercury 79. In a preferred embodiment depicted in FIG. 3, an upper capillary tube portion is shown as stainless steel tubing 75 which is secured to the upper end, or first end, of capillary 73, and is in contact with the mercury in the reservoir. As used herein, the word "tube" refers to a body having an elongated passageway. The upper end of the tubing functions as the valve seat. As a practical matter, the tubing is secured to the capillary by heating the first end of the capillary so as to expand the capillary bore, the tubing is then coated with an adhesive, such as epoxy cement, and inserted into the capillary. The tubing is secured by both the adhesive and the pressure-fit. Tubing 75 provides electrical continuity between the mercury in the reservoir and mercury in the capillary when the valve is closed, and also functions to absorb some of the vibrational force exerted by pull-rod 68 and gasket 70. The portion of the electrical circuit comprised of the mercury in reservoir 34, upper capillary portion 75 and the mercury in capillary 73 has a resistance essentially equal to the resistance of the mercury in the capillary. The lower end of mercury drop capillary 73 is constructed of chemically inert material. As used herein, the term "chemically inert" means chemically non-reactive with the environment to which the material is exposed. Examples of such materials are glasses, ceramics, glass ceramics, and polymers, among others.

The valve means includes valve stem 53 having lower and upper ends. The lower end includes a seal which acts in concert with the valve seat to open and close the valve. The upper end includes a ferromagnetic portion which is electromagnetically coupled with the actuating means. In a preferred embodiment illustrated in FIG. 3, the ferromagnetic portion is cylinder 56 which is secured to the upper end of pull-rod 68 and located within through-bore 58. The seal is shown as gasket 70 which is secured to the lower end of pull-rod 68. Gasket 70 is preferably constructed of rubber. Thus, it is seen that valve stem 53 includes cylinder 56, pull-rod 68, and gasket 70. The mass of the valve stem is less than 5 and preferably less than 3 grams. Gasket 70 is secured to the lower end of pull-rod 68. Flat spring 69 is secured to gasket 70 and spacers 72 and 47, and is biased so as to force gasket 70 to sealingly engage stainless steel tubing 75. Of course, biasing springs other than flat springs may be substituted to perform this function. Spacers 72 and 47 are operatively arranged to align gasket 70 with tubing 75. Spacers 72 and 47 are held in place by threaded element 57, which extends vertically through the through-bore of the spacers. Nut 37 functions to retain spacers 72 and 47 on threaded element 57. Alignment spring 98 is slidably engaged with spacer 72. The loop at the upper end of spring 98 is slidably engaged with pull-rod 68 and functions together with the position of cylinder 56 within through-bore 58 to align pull-rod 68 and gasket 70 with tubing 75. Mercury drops are dislodged from the lower, or second end, of capillary 73 by electromechanical drop knocker 78. Electrical terminal 38 is threadably engaged with lower end-cap 33 and is mechanically connected to threaded element 57 and spacers 72 and 47 to provide electrical continuity to the mercury.

The valve means of the present invention is said to be "fast-acting". In other words, the combined valve opening and closing time may be selected to be small enough to allow only enough mercury into the capillary to form a mercury drop having a surface area as low as $1 \times 10^{-2}$ cm$^2$ and preferably as low as $6 \times 10^{-3}$ cm$^2$ and even more preferably as low as $1 \times 10^{-4}$ cm$^2$.

Referring now to FIG. 4, upper end-cap 32 is bounded sequentially by inwardly-facing cylindrical surface 40, upwardly-facing annular surface 41, outwardly-facing cylindrical surface 42, upwardly-facing annular surface 43, inwardly-facing cylindrical surface 44, upwardly-facing annular surface 45, outwardly-facing cylindrical surface 46, downwardly-facing annular surface 48, inwardly-facing cylindrical surface 49, downwardly-facing annular surface 50, outwardly-facing cylindrical surface 51, and downwardly-facing annular surface 52. Surface 40 forms through-bore 58 which threadably engages adjustable ferromagnetic core 59. Surface 40 also includes annular recess 55 which holds O-ring 65. Ferromagnetic core 59 and ferromagnetic cylinder 56 are said to be electromagnetically coupled. In other words, ferromagnetic cylinder 56 which is positioned partially within through-bore 58 is electromagnetically attracted upwardly towards ferromagnetic core 59 when solenoid 60 is energized. The vertical travel of pull-rod 68 is limited by spacers 72 and 47.

As shown in FIGS. 3 and 4, surfaces 42-44 form annular recess 61 which holds coils 62 of solenoid 60. Solenoid 60 is energized by application of voltage pulses to lines 23 and 24. Ferromagnetic core 59 is threadably engaged within cylindrical recess 58. Thus, core 59 is adjustable in that it may be partially unscrewed from bore 58. This adjustability permits regulating the electromagnetic field strength and resulting force of attraction between core 59 and cylinder 56. O-ring 65 functions to seal the housing should the electrode be inverted. Referring to FIG. 3, it should be noted that the relatively high surface tension of mercury results in mercury not escaping through the normally small distance between cylinder 56 and cylindrical surface 40 when the electrode is inverted. This design feature enables the operator to invert the electrode and replace a broken capillary without spillage of mercury.

Again in reference to FIG. 3, valve assembly 76 comprises solenoid 60, adjustable ferromagnetic core 59, pull-rod 68, ferromagnetic cylinder 56, flat spring 69, gasket 70, support 71, spacers 72 and 47, and tubing 75. Cylinder 56, gasket 70, pull-rod 68 and flat spring 69 comprise valve stem 53. The relatively low mass of valve stem 53 enables rapid opening and closing of the valve. The inertia of valve stem 53 is minimized by isolating, or separating, elements 56, 68, and 70 from the relatively high mass core 59.

Once again, referring to FIG. 4, lower end-cap 33 is bounded sequentially by inwardly-facing cylindrical surface 80, upwardly-facing annular surface 81, inwardly-facing cylindrical surface 82, upwardly-facing annular surface 83, outwardly-facing cylindrical surface 84, and downwardly-facing annular surface 85. Sidewall 36 of housing 31 is threadably secured to surface 82 of lower end-cap 33. Surface 80 forms through-bore 86 which holds ferrule 74. Threaded through-bore 99 extends vertically between surfaces 85 and 81, and threadably engages threaded element 57.

Ferrule 74 is bounded sequentially by inwardly-facing cylindrical surface 90, upwardly-facing annular surface 91, outwardly-facing cylindrical surface 92, upwardly-facing annular surface 93, outwardly-facing cylindrical surface 94, and downwardly-facing annular surface 95. Ferrule 7 is secured to lower end-cap 33 such that surface 92 threadably engages surface 80. Surface 90 forms through-bore 96, which holds capillary 73.

Mercury drop capillary 73, which is typically made of glass, is inserted into through-bore 96 of ferrule 74. Through-bore 97 provides the means whereby mercury exits reservoir 34 to form mercury drops at the lower end of capillary 73. Conductive tubing 75 is secured within through-bore 97 by any suitable means, such as by epoxy cement.

Figure 4A:
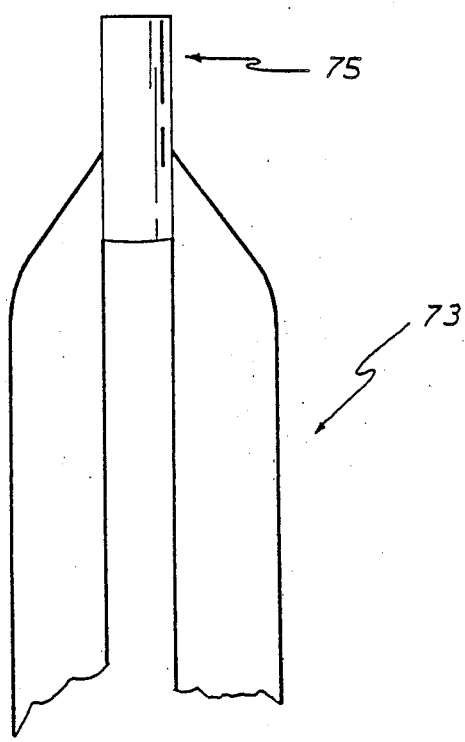
FIG. 4A is a magnified view of the upper or first end of the mercury drop capillary of the invention.
Figure 4:
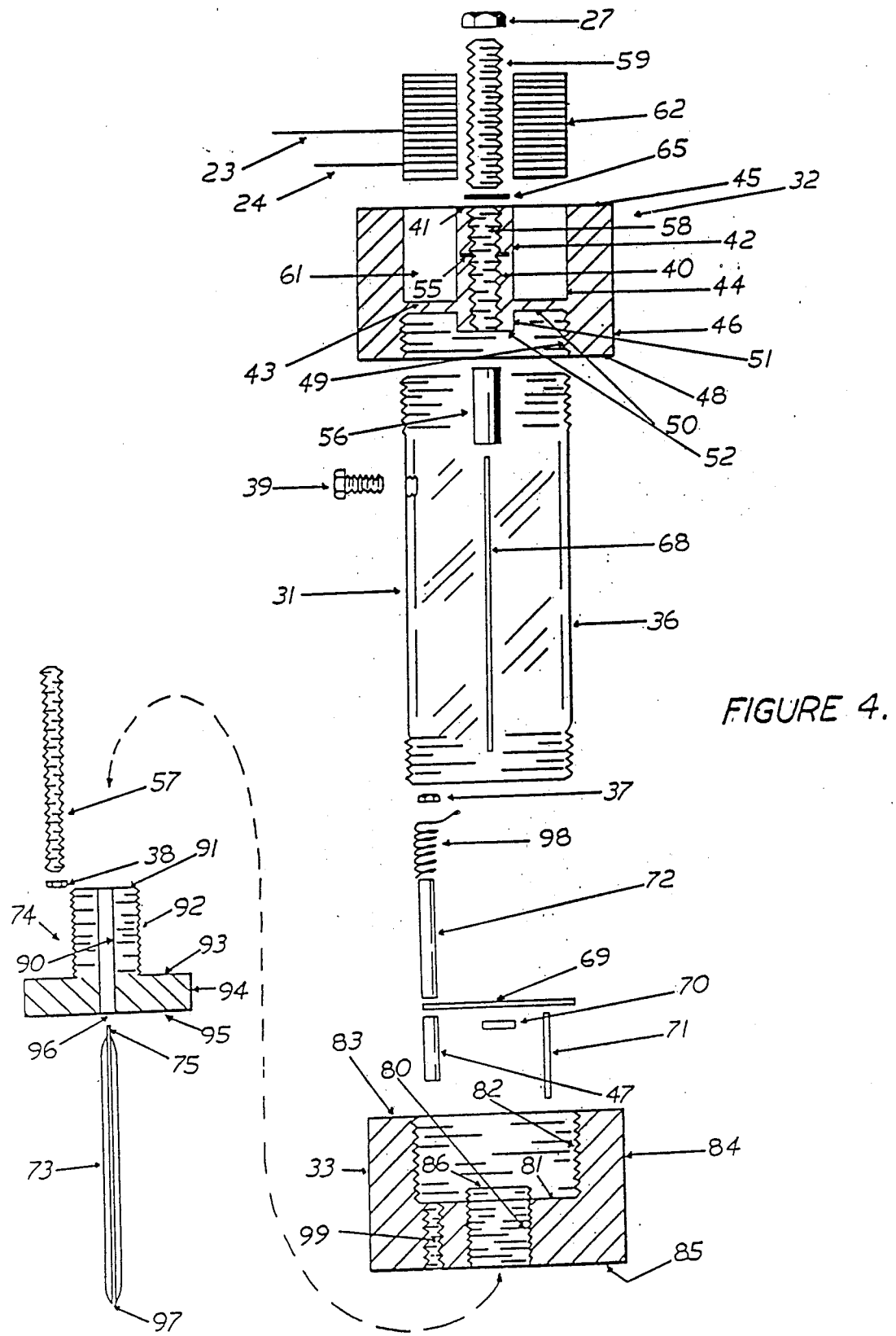
FIG. 4 is an exploded sectional view of the controlled-growth mercury drop electrode illustrated in FIG. 3.

FIG. 4A is a magnified view of tubing 75 and capillary 73. As shown in FIG. 4A, tubing 75 is inserted into the upper, or first end, of capillary 73.

Referring now to FIGS. 3 and 4, controlled-growth mercury electrode 30 receives electrical pulses via lines 23 and 24. The timing of drop formation is controlled by these electrical pulses. The coil 62 of solenoid 60 is energized (valve open) for times $t_{l,n}$ and closed during subsequent pulses $t_{2,n}$. Thus, the sequence of pulses $t_{1,1}$, $t_{2,1}$, $t_{1,2}$, $t_{2,2}$, ..., $t_{l,m}$. The times $t_{l,n}$ are related by $t_{l,n+l} = t_{l,n} + o$ and times $t_{2,n}$ by $t_{2,n+l} = t_{2,n}\delta$. These times may be selected arbitrarily over the ranges (milliseconds) $20 \leq t_{l,n}$, $\delta$, $\delta' \leq 20$ milliseconds.

When solenoid 60 is energized, core 59 becomes magnetized, thereby attracting cylinder 56 upwardly. This attraction forces pull-rod 68 to move in an upward direction, thereby causing gasket 70 to move away from tubing 75 and allowing mercury to flow into capillary 73. When solenoid 60 is not energized, flat spring 69 biases gasket 70 into sealing engagement with tubing 75, thereby preventing mercury from flowing into capillary 73.

The present invention was tested in the laboratory using analytical reagent grade chemicals. The experiments were conducted using 0.1 mM Cd(II) in 1 M NaNO$_3$ and the solutions were deaerated with purified argon gas for at least thirty minutes before experiment. The electrode was tested in both the hanging mercury drop mode and the dropping mercury mode The size of an emitted hanging mercury drop is directly proportional to the number of pulses and the duration of each pulse supplied to the solenoid. The maximum drop size depends upon the interfacial tension between the mercury and the glass, and between the mercury and solution. The interfacial tension in turn depends upon the diameter of the capillary through-bore, the nature of the electrolyte solution and depolarizer, and the potential applied to the electrode.

The present invention is capable of producing a wide range of drop sizes, merely by varying the pulse width and/or number of pulses. The rate of formation of the mercury drop is also controlled by varying the pulse width and/or number of pulses. For simplicity, the drop size may be described by specifying the number of pulses at a given pulse width. The maximum drop size obtainable for a given set of conditions is, of course, the size of the drop just prior to its becoming so large as to fall from the tip of the capillary by virtue of gravity. It is useful to specify this maximum drop size in terms of a maximum number of pulses, $P_{max}$, which can be applied to the solenoid before the drop is dislodged. Since the current changes abruptly when the drop is dislodged, it is possible to determine $P_{max}$ automatically simply by electronically monitoring the current while counting the pulses.

The determination of $P_{max}$ is useful for estimating quickly the relative size and variance of drops produced under different conditions (e.g., with different capillaries, different solenoid core adjustments, etc.). A high variance in $P_{max}$ may be an indication that the electrode requires maintenance. This feature is especially useful in applications involving unattended on-line monitoring processes.

Laboratory experiments confirm that drop size can be accurately estimated by specifying the number of pulses at a given pulse width. These experiments also illustrate the advantage of this estimation method. Using a capillary 12.5 centimeters in length with an internal bore diameter of 0.02 centimeter the variance in drop size was determined both by weighing drops and by electronically counting the number of pulses. In five replicate experiments, ten drops were produced (i.e., 10 energizing pulses with $t_{l,n}=20$ milliseconds and $t_{2,n}=100$ milliseconds). The weight of each drop was measured by a tedious and time-consuming process which involved collecting, drying, and individually weighing 10 drops. This physical measurement process resulted in a determination of an average weight of 10 drops equal to 24.82 milligrams with relative standard deviation of 1.8%. Similarly, electronic measurements which were completely automatic, consumed very little time, and no labor, indicated that the average number of pulses for maximum drop size was 27.48 with a relative standard deviation of 2.4%.

Variation of the pulse width and number of pulses enables production of a wide range of pulse sizes. In a square wave voltammetric experiment in which the net peak current for reduction of 0.1 mM Cd(II) was plotted against the number of energizing pulses raised to the two-thirds power, a straight-line slope was obtained for drop areas ranging from approximately $6 \times 10^{-3}$ cm$^2$ to $7.2 \times 10^{-2}$ cm$^2$, which were generated by 2–40 energizing pulses, each of 20 milliseconds pulse width. (The surface area of the drop is proportional to its mass raised to the two-thirds power.) This wide drop size range in conjunction with fine control of drop size enables adjustment of current response during unattended monitoring. This feature is useful in anodic stripping, where larger drop sizes can be used to dilute the amalgam phase at higher concentrations. This feature also renders possible a true area step experiment, wherein the area of an electrode at equilibrium or steady state is changed quickly by small increments.

In the dropping mercury mode transient current is measured in the hydrodynamic regime during growth of the drop. Because the response time is fast, the resistance is small and constant, and the increment of mercury added to the drop can be controlled, this current transient is reproducible.

Figure 5:
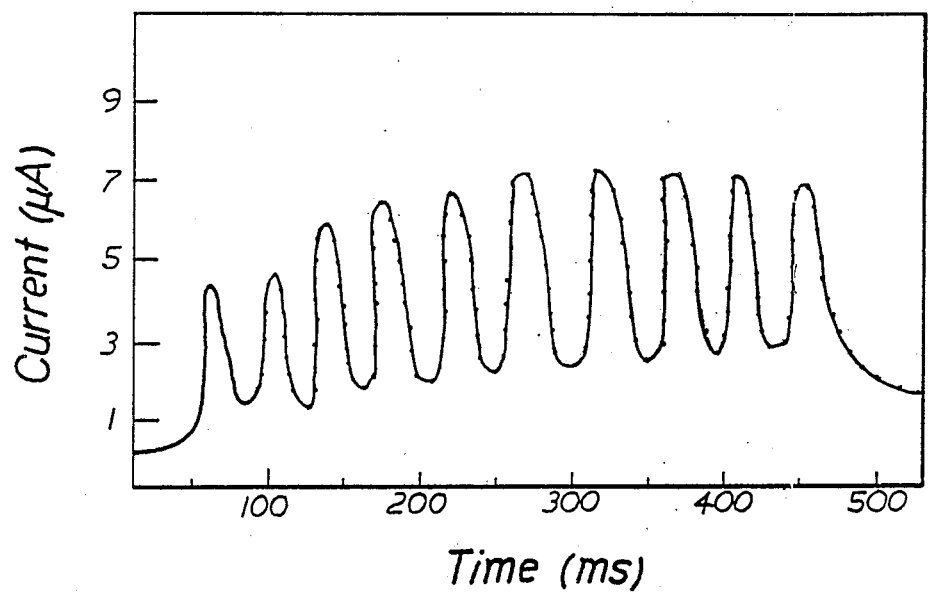
FIG. 5 is a current-time transient plot obtained using the present invention.

An experiment was run in which the electrode was held at a potential where Cd(II) is reduced at the diffusion-controlled rate and the energizing pulses, $t_{l,n}$, were 20 milliseconds, the valve was closed, $t_{2,n}$, for 20 milliseconds, $n=1,\ldots,10$, and $\delta=\delta'=0$. As shown in FIG. 5, the current changes smoothly with time as the drop grows and the shape of the current-time transient is the same for each increment of area. (The initial delay of about 15 milliseconds before current flows is the response time of the solenoid.) In particular, the first maximum current, which occurs at about 35 milliseconds, depends on concentration, though it also depends on the nature of the capillary and valve system. Thus, the transient measurement may be used with appropriate calibration to measure concentration.

FIG. 5 also shows clearly that the waiting time required for the drop and surrounding solution to stabilize is as little as 80 milliseconds for the smallest drop size. Thus, the electrode may be operated in the hanging drop mode at a repetition rate of about 80 milliseconds. The rate of formation and stabilization of the mercury drop may be controlled within the range of 50 to 500 milliseconds. This may be contrasted with the rate of 1–2s for a static mercury drop electrode, and thus can effect a ten-fold reduction in experiment time. This is a considerable experimental advantage when many drops are required for a single voltammogram.

In summary, it has been demonstrated experimentally that in comparison with the commercially available static mercury drop electrode, this electrode offers a smaller minimum size, finer gradation of size, wider range of size, faster response, shorter time for mechanical stabilization, and reproducible transient behavior before stabilization.

What is claimed is:

1. A mercury drop electrode comprising:
   a reservoir for liquid mercury;
   a mercury drop capillary having upper and lower open ends, said mercury drop capillary comprising a chemically inert lower capillary tube portion having a through-bore and an electrically conductive upper capillary tube portion supported by said lower portion and located partially within said through-bore, said upper capillary tube portion being in contact with merucry in said reservoir;
   valve means comprising a seal, and a valve seat acting in concert with said seal to close the valve, said seat comprising the upper end of the upper portion of said capillary;
   actuating means to lift said seal from said seat to allow mercury to enter said capillary from the reservoir and to lower said seal to said seat to prevent mercury from entering said capillary from the reservoir.

2. The electrode of claim 1 wherein the valve means further comprises a valve stem having lower and upper ends, said stem including the seal at the lower end and a ferromagnetic portion at its upper end and said actuating means comprising a solenoid proximate the ferromagnetic portion which acts to attract said ferromagnetic portion upwardly when said solenoid is energized, to lift said seal from said seat thus allowing mercury to enter said capillary from said reservoir.

3. The electrode of claim 2 wherein said actuating means further comprises a biasing spring to bias said seal against said seat when the solenoid is de-energized.

4. A mercury drop electrode as recited in claim 3 wherein said spring is a flat spring.

5. The electrode of claim 3 wherein the electrode further includes a control means for regulating the surface area of said mercury drops to at least five different values between $1 \times 10^{-4}$ cm$^2$ and $1 \times 10^{-1}$ cm$^2$.

6. A mercury drop electrode as recited in claim 2 wherein the valve stem comprises a pull-rod having first and second ends and a ferromagnetic cylinder secured to the rod first end and the seal is a gasket secured to the rod second end.

7. A mercury drop electrode as recited in claim 6 wherein said gasket is a rubber gasket.

8. A mercury drop electrode as recited in claim 2 wherein the mass of said valve stem is less than 5 grams.

9. A mercury drop electrode as recited in claim 2 wherein the solenoid has a core which is separate from said valve stem.

10. The electrode of claim 2 wherein the electrode, further includes a control means for regulating the surface area of said mercury drops to at least five different values between $1 \times 10^{-4}$ cm$^2$ and $1 \times 10^{-1}$ cm$^2$.

11. The electrode of claim 1 wherein the lower capillary tube portion comprises glass and the upper capillary tube portion is metal.

12. The electrode of claim 11 wherein the upper capillary tube portion is stainless steel.

13. The electrode of claim 12 wherein the electrode further includes a control means for regulating the surface area of said mercury drops to at least five different values between $1 \times 10^{-4}$ cm$^2$ and $1 \times 10^{-1}$ cm$^2$.

14. The electrode of claim 11 wherein the electrode further includes a control means for regulating the surface area of said mercury drops to at least five different values between $1 \times 10^{-4}$ cm$^2$ and $1 \times 10^{-1}$ cm$^2$.

15. The electrode of claim 1 wherein the reservoir is within a transparent housing.

16. A mercury drop electrode as recited in claim 1 wherein said electrode is arranged so that a mercury drop is adapted to be in contact with a fluid to be tested and an electrical circuit is provided which includes a path through mercury in said reservoir, said upper capillary tube portion, mercury in said capillary, and the mercury drop to the fluid, when said valve means is closed so as to prevent passage of mercury into said capillary.

17. A mercury drop electrode as recited in claim 16 wherein the portion of the electrical circuit comprised of said mercury in said reservoir, said upper capillary portion, and said mercury in said capillary has a resistance essentially equal to the resistance of the mercury in the capillary.

18. The mercury drop electrode of claim 1 wherein the electrode further includes a control means for regulating the surface area of said mercury drops to at least five different values between $1 \times 10^{-4}$ cm$^2$ and $1 \times 10^{-1}$ cm$^2$.

19. The electrode of claim 18 wherein the mercury drops are regulated to a size between $6 \times 10^{-3}$ cm$^2$ and $8 \times 10^{-2}$ cm$^2$.

20. The electrode of claim 18 wherein said control means includes computer-controlled timed electrical impulses to the actuating means to control open time of the valve means.

21. The electrode of claim 18 wherein said control means comprises a pulse sequencer arranged to provide electrical pulses to the actuating means to control open time of the valve means.

22. The electrode of claim 18 wherein the control means additionally controls the rate of formation of the mercury drop.

23. The electrode of claim 22 wherein the control means controls the rate of formation and stabilization of the mercury drop in the range of 50 to 500 milliseconds.

24. The electrode of claim 22 wherein the control means controls the rate of formation and stabilization of the mercury drop in the range of 75 to 300 milliseconds.

25. The mercury drop electrode of claim 1 wherein the electrode further includes a control means for regulating the surface area of said mercury drops to at least ten different values between $1 \times 10^{-4}$ cm$^2$ and $1 \times 10^{-1}$ cm$^2$.

26. The electrode of claim 25 wherein the control means additionally controls the rate of formation of the mercury drop.

27. The mercury drop electrode of claim 1 wherein the electrode further includes a control means regulating the surface area of mercury drops to any selected value between $1 \times 10^{-4}$ cm$^2$ and $1 \times 10^{-1}$ cm$^2$.

28. The electrode of claim 27 wherein the control means additionally controls the rate of formation of the mercury drop.

29. The electrode of claim 1 wherein the electrode may be physically inverted without spillage of mercury.

* * * * *